United States Patent
Shen et al.

(10) Patent No.: US 12,322,478 B2
(45) Date of Patent: Jun. 3, 2025

(54) METHOD AND APPARATUS FOR ACQUIRING GENE INFORMATION OF PROPRIETARY CLOUD CONTAINER CLUSTER

(71) Applicants: Beijing JingDong ShangKe Information Technology Co., Ltd., Beijing (CN); Beijing Jingdong Century Trading Co., Ltd., Beijing (CN)

(72) Inventors: Bowei Shen, Beijing (CN); Dayong Wang, Beijing (CN); Shi Bai, Beijing (CN)

(73) Assignees: Beijing JingDong ShangKe Information Technology Co., Ltd., Beijing (CN); Beijing Jingdong Century Trading Co., Ltd., Beijing (CN)

(*) Notice: Subject to any disclaimer, the term of this patent is extended or adjusted under 35 U.S.C. 154(b) by 131 days.

(21) Appl. No.: 18/247,227

(22) PCT Filed: Oct. 12, 2021

(86) PCT No.: PCT/CN2021/123280
§ 371 (c)(1),
(2) Date: Mar. 29, 2023

(87) PCT Pub. No.: WO2022/078326
PCT Pub. Date: Apr. 21, 2022

(65) Prior Publication Data
US 2023/0420083 A1    Dec. 28, 2023

(30) Foreign Application Priority Data
Oct. 13, 2020 (CN) .......................... 202011093261.4

(51) Int. Cl.
*H04L 41/08* (2022.01)
*G06F 16/901* (2019.01)
(Continued)

(52) U.S. Cl.
CPC ......... *G16B 50/30* (2019.02); *G06F 16/9027* (2019.01); *G06F 16/904* (2019.01); *G16B 45/00* (2019.02); *H04L 41/08* (2013.01)

(58) Field of Classification Search
None
See application file for complete search history.

(56) References Cited

U.S. PATENT DOCUMENTS

| | | | |
|---|---|---|---|
| 8,495,611 B2 | 7/2013 | Mccarthy et al. | |
| 9,137,106 B2 | 9/2015 | Mccarthy et al. | |

(Continued)

FOREIGN PATENT DOCUMENTS

| | | |
|---|---|---|
| CN | 102681899 A | 9/2012 |
| CN | 106603592 | 4/2017 |

(Continued)

OTHER PUBLICATIONS

Office Action received in corresponding Japan patent application 2023-518800, Jun. 5, 2024, and English Translation (6 pages).

(Continued)

*Primary Examiner* — Philip Wang
(74) *Attorney, Agent, or Firm* — HSML P.C.

(57) ABSTRACT

Provided is a method and an apparatus for acquiring a gene information of a proprietary cloud container cluster, the method includes: acquiring and analyzing a system hierarchical information, an association relationship information and a dependency relationship information of a module or a component of a proprietary cloud server cluster; generating a set of a gene information of a proprietary cloud container cluster through the acquired system hierarchical informa- (Continued)

tion, the association relationship information and the dependency relationship information of the module or the component, and performing an integrity verification on the set of the gene information of the proprietary cloud container cluster; and storing the set of the gene information of the proprietary cloud container cluster and determining a version information of a gene of the proprietary cloud container cluster, in response to the integrity verification passing.

13 Claims, 12 Drawing Sheets

(51) Int. Cl.
*G06F 16/904* (2019.01)
*G16B 45/00* (2019.01)
*G16B 50/30* (2019.01)

(56) References Cited

U.S. PATENT DOCUMENTS

| | | | |
|---|---|---|---|
| 9,641,599 B2 | 5/2017 | Wesley et al. | |
| 9,934,279 B2 | 4/2018 | Kali et al. | |
| 10,218,778 B2 | 2/2019 | Wesley et al. | |
| 10,824,791 B2 | 11/2020 | Solis | |
| 2002/0087734 A1* | 7/2002 | Marshall | G06F 9/50 719/310 |
| 2003/0129660 A1 | 7/2003 | Zien et al. | |
| 2012/0066670 A1 | 3/2012 | Mccarthy et al. | |
| 2013/0282798 A1 | 10/2013 | Mccarthy et al. | |
| 2014/0304326 A1 | 10/2014 | Wesley et al. | |
| 2015/0067783 A1* | 3/2015 | Pulier | G06F 9/5072 726/3 |
| 2015/0089064 A1 | 3/2015 | Salle et al. | |
| 2015/0161214 A1 | 6/2015 | Kali et al. | |
| 2017/0168861 A1 | 6/2017 | Dhawan et al. | |
| 2017/0201578 A1 | 7/2017 | Wesley et al. | |
| 2017/0358434 A1 | 12/2017 | Matsuura et al. | |
| 2018/0088973 A1 | 3/2018 | Subhraveti | |
| 2019/0068445 A1 | 2/2019 | Chauhan et al. | |
| 2019/0266225 A1 | 8/2019 | Solis | |
| 2023/0367651 A1* | 11/2023 | Li | G06F 9/5077 |

FOREIGN PATENT DOCUMENTS

| | | | | |
|---|---|---|---|---|
| CN | 107479863 | | 12/2017 | |
| CN | 107479964 A | | 12/2017 | |
| CN | 109840533 | | 6/2019 | |
| CN | 111343016 | | 6/2020 | |
| CN | 112333003 | | 2/2021 | |
| CN | 112333003 A | * | 2/2021 | ......... G06F 11/1458 |
| CN | 112333004 | | 2/2021 | |
| CN | 113419818 A | * | 9/2021 | |
| CN | 113765688 A | * | 12/2021 | ........... H04L 41/082 |
| CN | 117544521 A | * | 2/2024 | |
| EP | 1318472 A2 | | 6/2003 | |
| JP | 2006-72856 A | | 3/2006 | |
| JP | 2013-534019 A | | 8/2013 | |
| JP | 2016-519824 A | | 7/2016 | |
| JP | 2016-539427 A | | 12/2016 | |
| JP | 2019-149160 A | | 9/2019 | |
| WO | WO-2012100092 A2 | * | 7/2012 | ............. G06F 21/53 |

OTHER PUBLICATIONS

International Search Report and Written Opinion, issued in the corresponding PCT Application No. PCT/CN2021/123280, dated Jan. 14, 2022, 11 pages.
Extended European Search Report, issued in the the corresponding European patent application No. 21879370.1, dated Oct. 1, 2024, 11 pages.

* cited by examiner

METHOD AND APPARATUS FOR ACQUIRING GENE INFORMATION OF PROPRIETARY CLOUD CONTAINER CLUSTER

CROSS REFERENCE TO RELATED APPLICATION

This application is a Section 371 National Stage Application of International Application No. PCT/CN2021/123280, filed on Oct. 12, 2021, entitled "METHOD AND APPARATUS FOR ACQUIRING GENE INFORMATION OF PROPRIETARY CLOUD CONTAINER CLUSTER", which claims priority to Chinese patent Application No. CN202011093261.4 filed on Oct. 13, 2020, the content of which are incorporated herein by reference in their entirety.

TECHNICAL FIELD

The present disclosure relates to a field of a computer technology, and in particular, to a method and an apparatus for acquiring a gene information of a proprietary cloud container cluster.

BACKGROUND

A proprietary cloud generally uses a hierarchical management architecture. A bottom layer supports a physical server cluster, and provides a cloud computing service to a user, etc. An application service provided by each product line in a proprietary cloud platform may be organized and managed by using a container cluster technology. At present, an information extraction for a proprietary cloud container cluster is mainly to solve an application migration between clusters with different structures, and may not analyze and display an extracted cluster container configuration information.

SUMMARY

In view of this, the present disclosure provides a method and an apparatus that may perform a quick and accurate extraction on an overall information that may comprehensively describe a container cluster and a service application contained in the container cluster.

An aspect of the present disclosure provides a method for acquiring a gene information of a proprietary cloud container cluster, including:
  acquiring and analyzing a system hierarchical information, an association relationship information and a dependency relationship information of a module or a component of a proprietary cloud server cluster;
  generating a set of a gene information of a proprietary cloud container cluster through the acquired system hierarchical information, the association relationship information and the dependency relationship information of the module or the component, and performing an integrity verification on the set of the gene information of the proprietary cloud container cluster; and
  storing the set of the gene information of the proprietary cloud container cluster and determining a version information of a gene of the proprietary cloud container cluster, in response to the integrity verification passing.
According to embodiments of the present disclosure, the method further includes: performing a visual display on all or part of genes of the proprietary cloud container cluster of the set of the gene information of the proprietary cloud container.

According to embodiments of the present disclosure, wherein the acquiring and analyzing a system hierarchical information of a module or a component of a proprietary cloud server cluster includes:
  acquiring and analyzing a basic system gene information of the proprietary cloud server cluster, and verifying the basic system gene information to generate a verification information;
  acquiring and analyzing a basic dependent gene information of the proprietary cloud server cluster, and verifying the basic dependent gene information to generate a verification information;
  acquiring and analyzing a product line static service tree gene information of the proprietary cloud server cluster, and verifying the product line static service tree gene information to generate a verification information; and
  performing a consistency and completeness verification on all acquired information, and generating, in response to the verification passing, a version information of the module or the component.

According to embodiments of the present disclosure, wherein the acquiring and analyzing a basic system gene information of the proprietary cloud server cluster and verifying the basic system gene information to generate a verification information includes:
  scanning the proprietary cloud server cluster through an out-of-band management system and an in-band management system to acquire a gene information of a physical server cluster, and performing a consistency and completeness verification on the gene information of the physical server cluster to generate a corresponding verification information;
  scanning the proprietary cloud server cluster through a cloud platform operation and maintenance management system to acquire an operating system and network topology information, and performing the consistency and completeness verification on the operating system and network topology information to generate a corresponding verification information; and
  scanning the proprietary cloud server cluster through the cloud platform operation and maintenance management system to acquire a cluster component information, and performing the consistency and completeness verification on the cluster component information to generate a corresponding verification information.

According to embodiments of the present disclosure, wherein the acquiring and analyzing a basic dependent gene information of the proprietary cloud server cluster and verifying the basic dependent gene information to generate a verification information includes:
  scanning the proprietary cloud server cluster through a cloud platform operation and maintenance management system to acquire a dependent component information of a proprietary cloud platform product line, and performing a consistency and completeness verification on the dependent component information to generate a corresponding verification information.

According to embodiments of the present disclosure, wherein the acquiring and analyzing a product line static service tree gene information of the proprietary cloud server cluster and verifying the product line static service tree gene information to generate a verification information includes:

scanning the proprietary cloud server cluster through a proprietary cloud management platform and cluster management module to acquire an IaaS product component information of a proprietary cloud platform, and performing a consistency and completeness verification on the IaaS product component information to generate a corresponding verification information;

scanning the proprietary cloud server cluster through the proprietary cloud management platform and cluster management module to acquire a PaaS product component information of the proprietary cloud platform, and performing the consistency and completeness verification on the PaaS product component information to generate a corresponding verification information; and scanning the proprietary cloud server cluster through the proprietary cloud management platform and cluster management module to acquire a SaaS product component information of the proprietary cloud platform, and performing the consistency and completeness verification on the SaaS product component information to generate a corresponding verification information.

According to embodiments of the present disclosure, wherein the acquiring and analyzing an association relationship information of a module or a component of a proprietary cloud server cluster includes:

scanning an IaaS product line, a PaaS product line and a SaaS product line of a proprietary cloud platform product line static service tree to acquire all proprietary cloud products of the IaaS product line, the PaaS product line and the SaaS product line;

analyzing the proprietary cloud product to determine an application grouping corresponding to the proprietary cloud product; and determining a creation unit of the application grouping, and determining a device allocation information and an arrangement information of a corresponding container according to the creation unit, wherein the creation unit is a mirror-image package or a program package.

According to embodiments of the present disclosure, wherein the acquiring and analyzing a dependency relationship information of a module or component of a proprietary cloud server cluster includes:

scanning an IaaS product line, a PaaS product line and a SaaS product line of a proprietary cloud platform product line static service tree to acquire all proprietary cloud products of the IaaS product line, the PaaS product line and the SaaS product line;

determining, according to a reference statement contained in a program code, a reference statement of a configuration file, and a dependent component information for data reading and writing, an underlying function module information on which an application program of each proprietary cloud product related service depends and a function module information of a product having a dependency relationship with the application program, so as to acquire a dependency relationship;

generating, for each module or component, a set of corresponding dependent modules or dependent components; and analyzing a dependency hierarchy of the module or component according to the dependency relationship.

According to embodiments of the present disclosure, wherein storing the system hierarchical information includes:

storing the system hierarchical information to a first database in order of a basic system gene information, a basic dependent gene information and a product line static service tree gene information;

storing the association relationship information to a second database based on a tree data structure; and storing the dependency relationship information in a third database.

According to embodiments of the present disclosure, wherein the performing a visual display on all or part of genes of the proprietary cloud container cluster of the set of the gene information of the proprietary cloud container includes:

displaying the system hierarchical information of the proprietary cloud server cluster in order of a basic system gene information, a basic dependency gene information, and a product line static service tree gene information, wherein the system hierarchical information includes a name, a function, a technical indicator, and a basic status information of the module or the component;

displaying a service directory tree of the association relationship information by using a tree structure, and displaying a Pod information, a container information, and an application grouping information of the module or the component; and displaying, through a dependency hierarchical structure, a name and a status of each component of all dependency hierarchies in a proprietary cloud platform and a module and a component on which the module or the component depends, and displaying a module or component for which the module or the component provides a support.

According to another aspect of the present disclosure, an apparatus for acquiring a gene information of a proprietary cloud container cluster is provided, including:

an information acquisition and analysis module configured to acquire and analyze a system hierarchical information, an association relationship information and a dependency relationship information of a module or a component of a proprietary cloud server cluster;

a verification module configured to generate a set of a gene information of the proprietary cloud container cluster through the acquired system hierarchical information, the association relationship information and the dependency relationship information of the module or the component, and perform an integrity verification on the set of the gene information of the proprietary cloud container cluster; and a storage and version management module configured to store the set of the gene information of the proprietary cloud container cluster and determine a version information of a gene of the proprietary cloud container cluster, in response to the integrity verification passing.

According to embodiments of the present disclosure, the apparatus further includes:

a display module configured to perform a visual display on all or part of genes of the proprietary cloud container cluster of the set of the gene information of the proprietary cloud container.

According to another aspect of the present disclosure, an electronic device is provided, including:

one or more processors;

a storage apparatus configured to store one or more programs, wherein the one or more programs, when executed by the one or more processors, cause the one or more processors to implement the method for acquiring a gene information of a proprietary cloud container cluster as described above.

According to another aspect of the present disclosure, a computer-readable storage medium having executable instructions stored thereon is provided, and the instructions, when executed by a processor, cause the processor to implement the method for acquiring a gene information of a proprietary cloud container cluster as described above.

BRIEF DESCRIPTION OF THE DRAWINGS

The above and other objectives, features, and advantages of the present disclosure will be clearer through the following description of embodiments of the present disclosure with reference to the drawings, in which.

DETAILED DESCRIPTION OF EMBODIMENTS

Figure 1A:
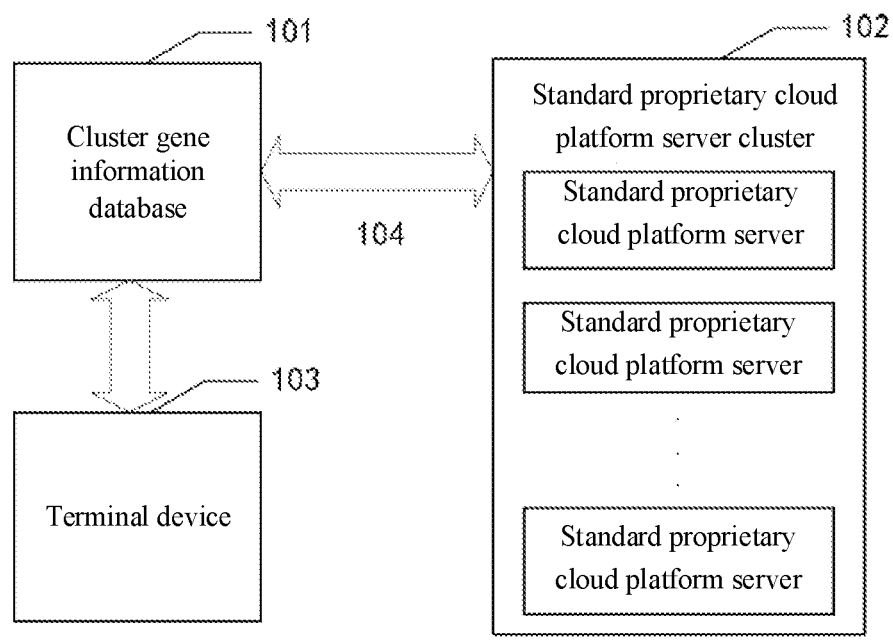
FIG. 1a schematically shows an exemplary system architecture to which a method and an apparatus for acquiring a gene information of a proprietary cloud container cluster may be applied according to an embodiment of the present disclosure.

Embodiments of the present disclosure will be described below with reference to the accompanying drawings. It should be understood, however, that these descriptions are merely exemplary and are not intended to limit the scope of the present disclosure. In the following detailed descriptions, for the ease of explanation, many specific details are set forth to provide a comprehensive understanding of embodiments of the present disclosure. However, it is obvious that one or more embodiments may also be implemented without the specific details. In addition, in the following descriptions, descriptions of well-known structures and technologies are omitted to avoid unnecessarily obscuring the concept of the present disclosure.

Terms used herein are only intended to describe specific embodiments and are not intended to limit the present disclosure. Terms "including", "containing", etc. used herein indicate the presence of the described features, steps, operations and/or components, but do not exclude the presence or addition of one or more other features, steps, operations and/or components.

All terms (including technical and scientific terms) used herein have meanings generally understood by those of ordinary skilled in the art, unless otherwise defined. It should be noted that the terms used herein should be interpreted as having the meaning consistent with the context of the present disclosure, and should not be interpreted in an idealized or overly rigid manner.

In a case that an expression similar to "at least one selected from A, B, or C" is used, the expression should generally be interpreted according to the meaning of the expression generally understood by those of ordinary skilled in the art (for example, "a system having at least one selected from A, B, or C" shall include, but is not limited to, a system having A alone, having B alone, having C alone, having A and B, having A and C, having B and C, and/or having A, B and C, etc.)

Embodiments of the present disclosure provide a method for acquiring a gene information of a proprietary cloud container cluster, including: acquiring and analyzing a system hierarchical information, an association relationship information and a dependency relationship information of a module or a component of a proprietary cloud server cluster; generating a set of a gene information of a proprietary cloud container cluster through the acquired system hierarchical information, the association relationship information and the dependency relationship information of the module or the component, and performing an integrity verification on the set of the gene information of the proprietary cloud container cluster; and storing the set of the gene information of the proprietary cloud container cluster and determining a version information of a gene of the proprietary cloud container cluster, in response to the integrity verification passing.

Since all containers in a cluster needs to be packaged in a unified manner each time a proprietary cloud cluster is closed, many information in the cluster is solidified. In the present disclosure, a container information acquisition of a proprietary cluster may be automatically implemented by using a cluster-container-based gene information extraction technology, and an accurate and effective information acquired may be ensured.

FIG. 1a schematically shows an exemplary system architecture to which a method and an apparatus for acquiring a gene information of a proprietary cloud container cluster may be applied according to an embodiment of the present disclosure. It should be noted that FIG. 1a is only an example of a system architecture to which embodiments of the present disclosure may be applied, so as to help those skilled in the art understand the technical content of the present disclosure, but it does not mean that embodiments of the present disclosure may not be applied to other devices, systems, environments or scenarios.

As shown in FIG. 1a, a system architecture 100 according to the embodiment may include a cluster gene information database 101, a standard proprietary cloud platform server cluster 102, a terminal device 103 and a network 104. The network 104 is a medium used to provide a communication link between the cluster gene information database 101, the standard proprietary cloud platform server cluster 102, and the terminal device 103. The network 104 may include various connection types, such as wired and wireless communication links, optical fiber cables, etc.

The cluster gene information database 101 is used to store a cluster gene information obtained from the standard proprietary cloud platform server cluster 102. The standard proprietary cloud platform refers to a proprietary cloud platform environment that, after a long period of research and development and quality verification, ensures that a function, a performance, a stability, a scalability, a security and other technical indicators may meet requirements of technical standards. The cluster gene refers to a structured information that may completely represent a number, a configuration, a composition, data, an association relationship, a dependency relationship and other key information of each component in the cluster. An automatic creation and component deployment of the same or similar clusters may be implemented through the cluster gene. The cluster gene information database 101 may be a database server associated with the standard proprietary cloud platform server cluster 102. Alternatively, in other embodiments, the cluster gene information database 101 may also be configured as a server in the standard proprietary cloud platform server cluster 102.

The terminal device 103 may send a request information to the cluster gene information database 101 through the network 104 in response to a user operation, so as to acquire a gene information of a proprietary cloud container cluster that needs to be viewed or consulted through the response of the cluster gene information database 101. In an embodiment, the terminal device 103 may be various electronic devices with a processing function and installed with a client application, for example. The electronic devices include, but are not limited to, a smart phone, a tablet computer, a laptop computer, a desktop computer, etc. The installed client applications include, but are not limited to: a network communication application, a web browsing application, an online payment platform, etc. For example, the request information sent to the cluster gene information database 101 may be sent through an interface provided by the client application.

The cluster gene information database 101 and the standard proprietary cloud platform server cluster 102 are connected through the network 104. The cluster gene information database 101 may acquire a data information of the standard proprietary cloud platform server cluster 102 through the network 104, so that the acquired data may be used to implement a reconstruction of the standard proprietary cloud platform, for example. Exemplarily, based on a K8S technology and characteristics of a container in a K8S cluster, a system of acquiring a gene information of the proprietary cloud container cluster may improve an efficiency of a cluster gene information and enable an extracted cluster gene information to be applied to a genetic replication and an upgrading of the cluster.

It should be noted that the method for acquiring a gene information of a proprietary cloud container cluster provided by embodiments of the present disclosure may generally be performed by the cluster gene information database 101. Accordingly, the apparatus for acquiring a gene information of a proprietary cloud container cluster provided by embodiments of the present disclosure may generally be provided in the cluster gene information database 101. The method for acquiring a gene information of a proprietary cloud container cluster provided by embodiments of the present disclosure may also be performed by a server or server cluster different from the cluster gene information database 101 and capable of communicating with the cluster gene information database 101. Accordingly, the apparatus for acquiring a gene information of a proprietary cloud container cluster provided by embodiments of the present disclosure may also be provided in the server or server cluster different from the cluster gene information database 101 and capable of communicating with the cluster gene information database 101.

It should be understood that the number of database, server, terminal device and network in FIG. 1a is only schematic. According to implementation needs, any number of servers and networks may be provided.

Figure 1B:
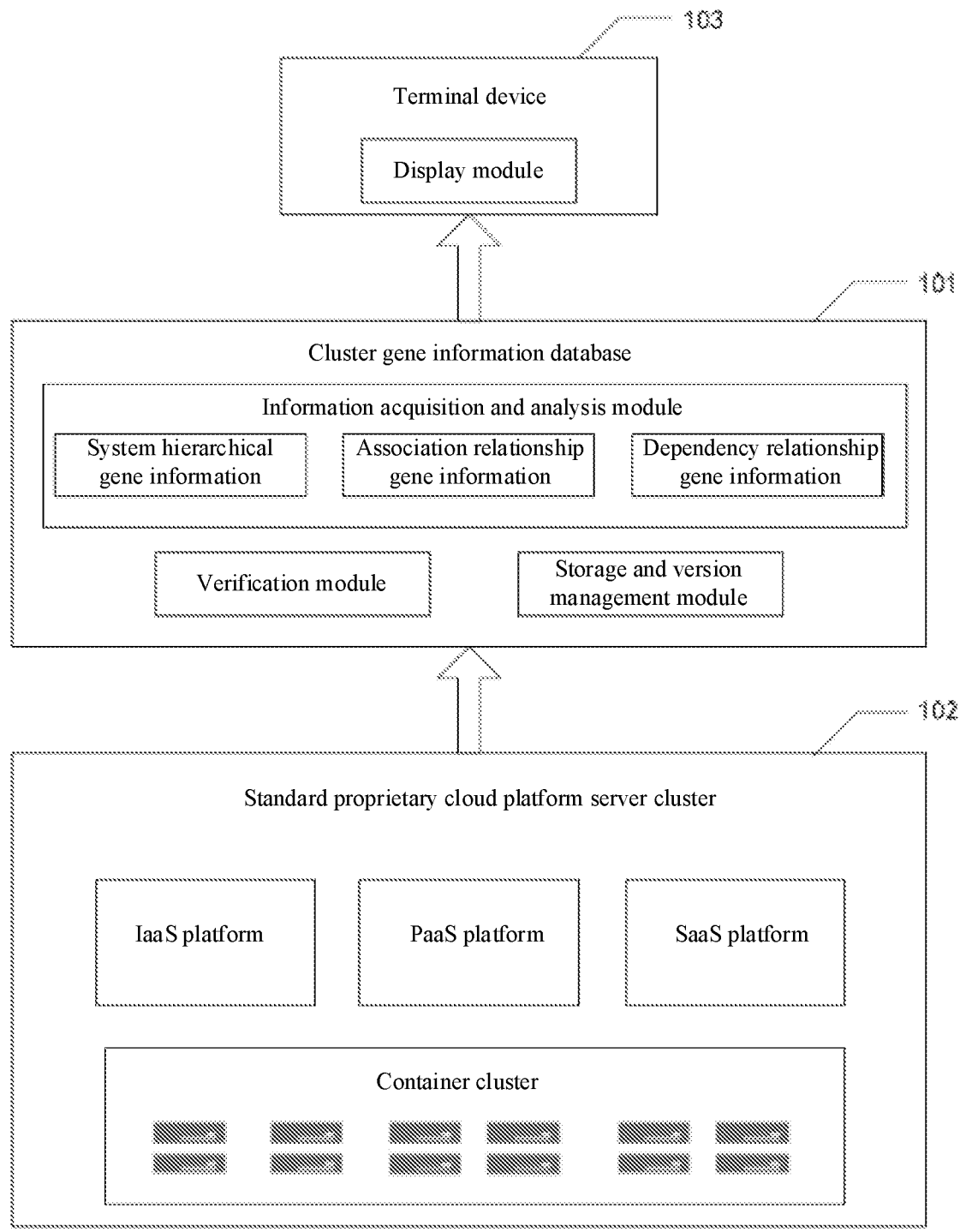
FIG. 1b schematically shows an implementation flow of a method and an apparatus for acquiring a gene information of a proprietary cloud container cluster according to an embodiment of the present disclosure.

FIG. 1B schematically shows an implementation flow of a method and an apparatus for acquiring a gene information of a proprietary cloud container cluster according to an embodiment of the present disclosure. According to embodiments of the present disclosure, a cluster gene information acquired from the standard proprietary cloud platform server cluster 102 is stored in the cluster gene database 101 and displayed on the terminal device 103.

In the embodiment, the cluster gene database 101 stores the cluster gene information comprehensively collected and gathered from the standard proprietary cloud platform. The cluster gene information includes information three dimensions: the first dimension is eight hierarchies of information that form a proprietary cluster, that is, a system hierarchical gene information, which implements a discrete and full coverage set of modules and components, and a composition analysis and an information collection of the modules and components are implemented through the system hierarchical gene information; the second dimension is an association relationship set of each module or component of a product line in the cluster, that is, an association gene information; and the third dimension is a dependency relationship set of each module or component in the product line of the cluster, that is, a dependency relationship gene information.

Based on the above-mentioned three dimensions, a complete set of the gene information of the proprietary cloud cluster may be formed. IaaS, PaaS and SaaS platforms and a container cluster are built in the standard proprietary cloud platform server cluster 102 by using the set of the gene information of the proprietary cloud cluster, and a reconstruction of the standard proprietary cloud platform is implemented. The IaaS is a cloud platform service layer that includes basic cloud resources such as a virtualized computing resource, a virtualized network resource, a virtualized storage resource, etc.; the PaaS is a cloud platform service layer that provides platform level cloud resources such as a database, a middleware, a development component, a big data component, etc.; and the SaaS is a cloud platform service layer that provides a software resource to support a specific business.

Figure 1C:
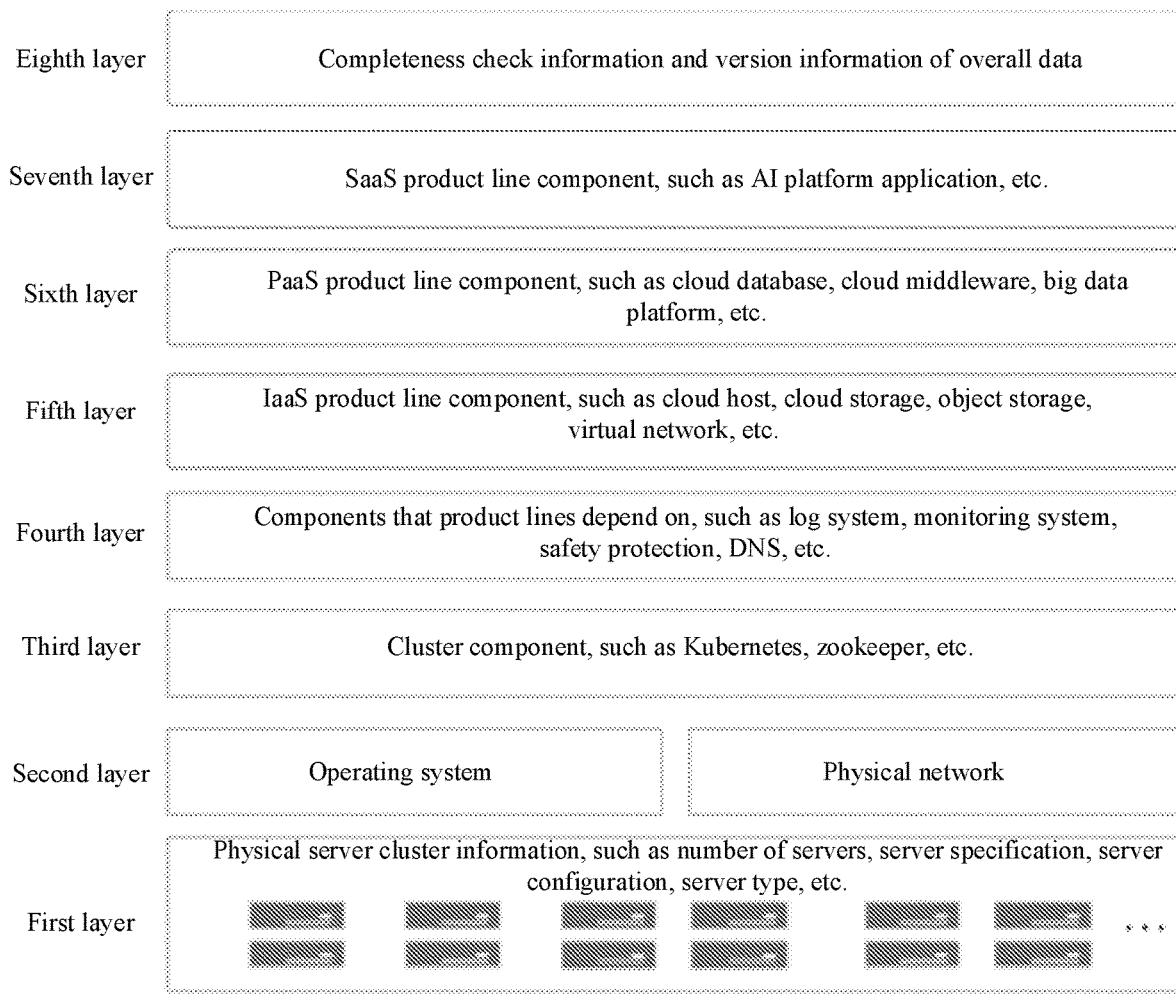
FIG. 1c shows a structural block diagram of a system hierarchical gene information of a proprietary cloud cluster according to an embodiment of the present disclosure.

FIG. 1c shows a structural block diagram of a system hierarchical gene information of a proprietary cloud cluster according to an embodiment of the present disclosure.

As shown in FIG. 1c, a proprietary cloud cluster system is divided into 8 cluster gene information hierarchies from the bottom up. First to third layers of cluster gene information is a basic system gene information. Specifically, the first layer of cluster gene information refers to an information collected by automatically scanning a gene information of a physical server cluster through an out-of-band management system and an in-band management system, such as the number of servers, a server specification, a server configuration, and a server type (a management node, a computing node, a storage node, etc.); the second layer of cluster gene information is an information collected by automatically scanning an information such as an operating system, a network topology, etc., of a service server through a cloud platform operation and maintenance management system; and the third layer of cluster gene information refers to a cluster component information scanned and collected through the cloud platform operation and maintenance management system, such as Kubernetes, zookeeper and other cluster components.

A fourth layer of cluster gene information is a basic dependency gene information, including an information collected by scanning and collecting an information of a component on which each product line on the proprietary cloud platform depends through the cloud platform operation and maintenance management system, such as a log system, a monitoring system, a security protection system, a DNS service, etc.

Fifth to seventh layers of cluster gene information is a product line static service tree gene information. Specifically, the fifth layer of cluster gene information is an information collected by scanning an IaaS product component information on the proprietary cloud platform through a proprietary cloud management platform and Kubernetes cluster management module, including a K8S service, a Pod, an API, a container, an application, a grouping, a container mirror image, etc. that support product components; the sixth layer of cluster gene information is an information collected by scanning a PaaS product component information on the proprietary cloud platform through the proprietary cloud management platform and Kubernetes cluster management module, including a virtual machine, a K8S service, a Pod, an API, a container, an application, a grouping, a container mirror image, etc. that support the product components; the seventh layer of cluster gene information is an information collected by scanning a SaaS product component information on the proprietary cloud platform through the proprietary cloud management platform and Kubernetes cluster management module, including a virtual machine, a virtual storage, a virtual network, a PaaS service, a K8S service, a Pod, an API, a container, an application, a grouping, a container mirror image, etc. that support the product components.

An eighth layer of cluster gene information is an information collected by performing a consistency and completeness verification on all collected information, and generating a corresponding verification information and a version information of the module or component. Exemplarily, the version information is determined based on an automatic generation rule of a version, such as an auto increment of a small-version version information, etc.; alternatively, the version information is determined manually, and the version information of a gene information of each module and component of the cluster is generated.

Through the system for acquiring a gene information of a proprietary cloud container cluster according to embodiments of the present disclosure, an automatic acquisition of the proprietary cloud cluster container information may be implemented, and an accuracy and an effectiveness of an acquired information may be ensured.

Figure 2:
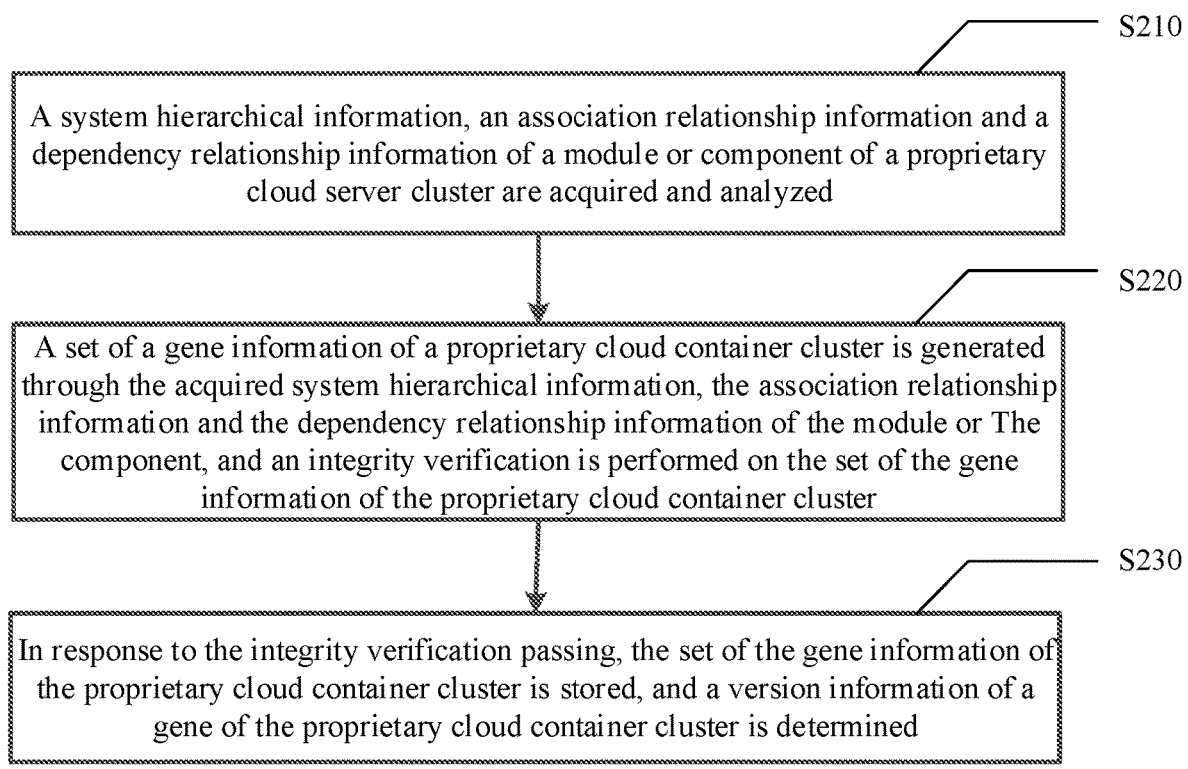
FIG. 2 schematically shows a flowchart of a method for acquiring a gene information of a proprietary cloud container cluster according to an embodiment of the present disclosure.

FIG. 2 schematically shows a flowchart of a method for acquiring a gene information of a proprietary cloud container cluster according to an embodiment of the present disclosure.

As shown in FIG. 2, the method includes extracting a gene information of a container cluster from three dimensions of a system hierarchical information, an association relationship information and a dependency relationship information, and verifying and storing the gene information of the container cluster. Specifically, the method includes operations S210 to S230.

In operation S210, a system hierarchical information, an association relationship information and a dependency relationship information of a module or component of a proprietary cloud server cluster are acquired and analyzed.

In operation S220, a set of the gene information of the proprietary cloud container cluster is generated through an acquired system hierarchical information, an acquired association relationship information and an acquired dependency relationship information of the module or component, and an integrity verification is performed on the set of the gene information of the proprietary cloud container cluster.

In operation S230, in response to the integrity verification passing, the set of the gene information of the proprietary cloud container cluster is stored, and a version information of a proprietary cloud container cluster gene is determined.

The method shown in FIG. 2 will be further described below with reference to specific embodiments.

Figure 3:
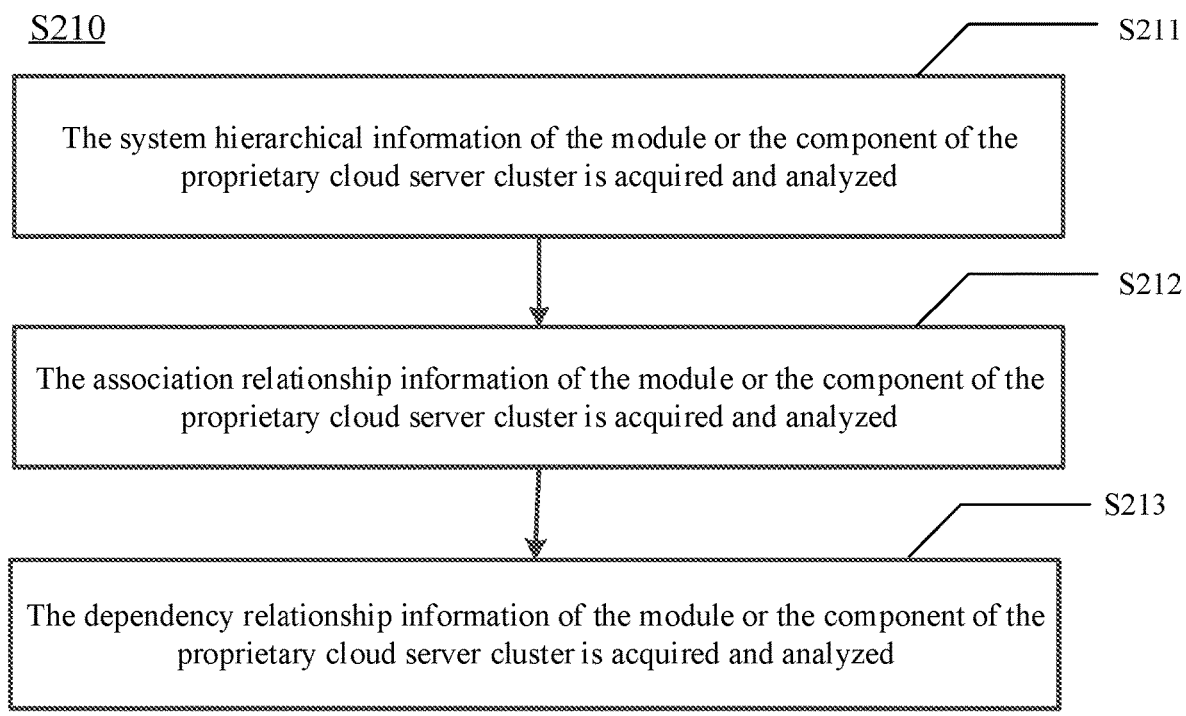
FIG. 3 schematically shows a flowchart of a method for acquiring and analyzing a cluster gene information of three dimensions of a module or component of a proprietary cloud server cluster according to an embodiment of the present disclosure.

FIG. 3 schematically shows a flowchart of a method for acquiring and analyzing a cluster gene information of three dimensions of a module or component of a proprietary cloud server cluster according to an embodiment of the present disclosure.

As shown in FIG. 3, operation S210 includes operations S211 to S213. First, in operation S211, the system hierarchical information of the module or component of the proprietary cloud server cluster is acquired and analyzed, a detailed information of various modules and components such as a product line, a system, a module, a service, an application, a grouping, and an instance at a plurality of hierarchies in the standard proprietary cloud platform is analyzed and collected, and an automatic system generation module that may express and reconstruct the system hierarchical information is created for each module and component. The system hierarchical information includes a basic system gene information, a basic dependency gene information and a product line static service tree gene information.

Figure 4:
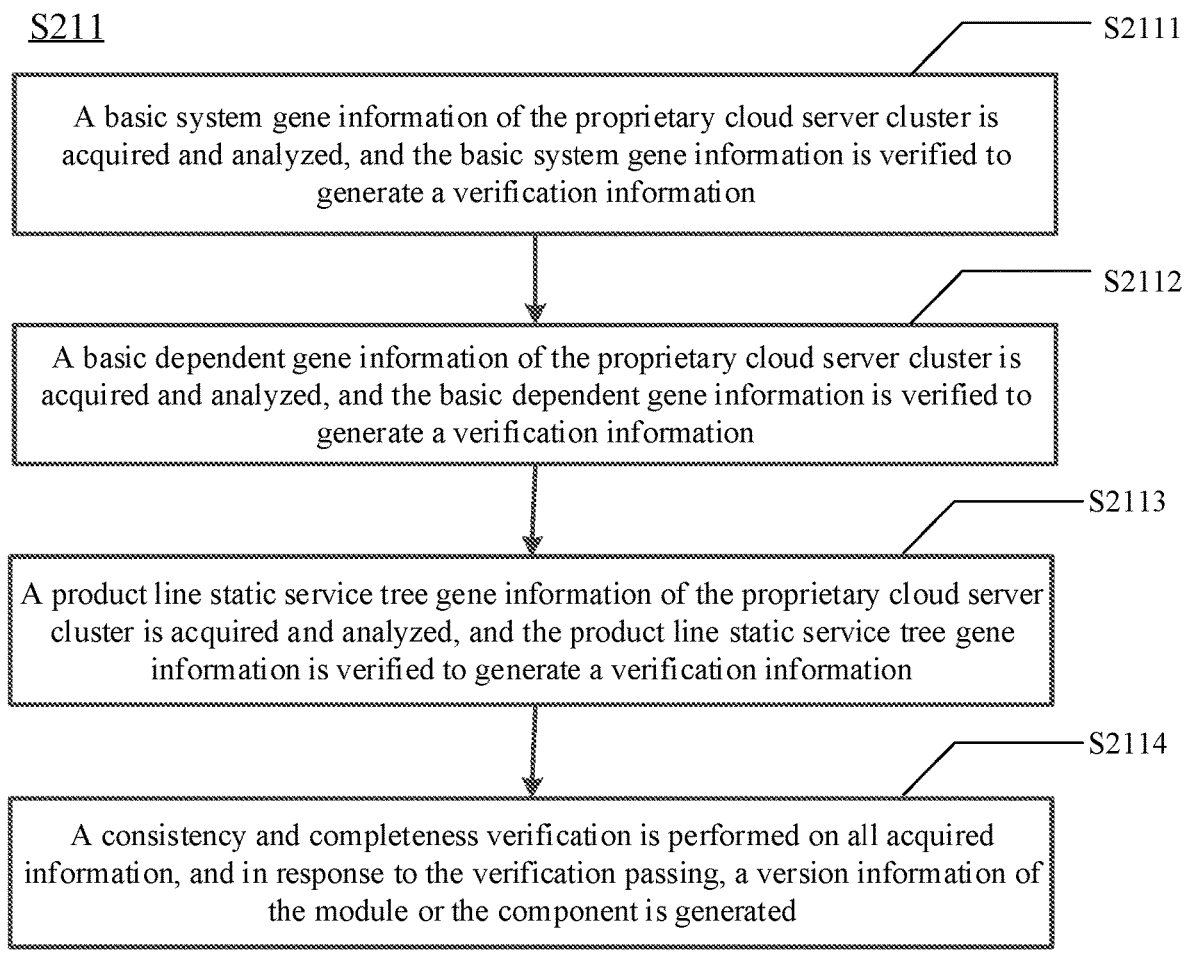
FIG. 4 schematically shows a flowchart of a method for acquiring and analyzing a system hierarchical information of a module or component of a proprietary cloud server cluster according to an embodiment of the present disclosure.

FIG. 4 schematically shows a flowchart of a method for acquiring and analyzing a system hierarchical information of a module or component of a proprietary cloud server cluster according to an embodiment of the present disclosure.

As shown in FIG. 4, operation S211 includes operations S2111 to S2114.

In operation S2111, a basic system gene information of the proprietary cloud server cluster is acquired and analyzed, and the basic system gene information is verified to generate a verification information. Specifically, the acquiring and analyzing a basic system gene information of a proprietary cloud server cluster, and verifying the basic system gene information to generate a verification information includes the following operations.

The proprietary cloud server cluster is scanned through an out-of-band management system and an in-band management system to acquire a gene information of a physical server cluster, and a consistency and completeness verification is performed on the gene information of the physical server cluster to generate a corresponding verification information. The gene information of the physical server cluster includes, for example, the number of servers, a server specification, a server configuration, a server type, a management node, a computing node, a storage node, etc.

The proprietary cloud server cluster is scanned through a cloud platform operation and maintenance management system to acquire an operating system and network topology information, and the consistency and completeness verification is performed on the operating system and network topology information to generate a corresponding verification information.

The proprietary cloud server cluster is scanned through the cloud platform operation and maintenance management system to acquire a cluster component information, and the consistency and completeness verification is performed on the cluster component information to generate a corresponding verification information. The cluster component information includes Kubernetes, zookeeper and other cluster components.

In operation S2112, a basic dependent gene information of the proprietary cloud server cluster is acquired and analyzed, and the basic dependent gene information is verified to generate the verification information.

Specifically, in operation S2112, the proprietary cloud server cluster is scanned through a cloud platform operation and maintenance management system to acquire a dependent component information of a proprietary cloud platform product line, and the consistency and completeness verification is performed on the dependent component information to generate a corresponding verification information. The dependent component information includes, for example, a log system, a monitoring system, a security protection system, a DNS service, etc.

In operation S2113, a product line static service tree gene information of the proprietary cloud server cluster is acquired and analyzed, and the product line static service tree gene information is verified to generate the verification information. Specifically, the acquiring and analyzing a product line static service tree gene information of the proprietary cloud server cluster, and verifying the product line static service tree gene information to generate the verification information includes the following operations.

The proprietary cloud server cluster is scanned through a proprietary cloud management platform and cluster management module to acquire an IaaS product component information of a proprietary cloud platform, including a K8S service, a Pod, an API, a container, an application, a grouping, a container mirror image, etc. that support product components, and a consistency and completeness verification is performed on the IaaS product component information to generate a corresponding verification information.

The proprietary cloud server cluster is scanned through the proprietary cloud management platform and cluster management module to acquire a PaaS product component information of the proprietary cloud platform, including a virtual machine, a K8S service, a Pod, an API, a container, an application, a grouping, a container mirror image, etc. that support the product components, and the consistency and completeness verification is performed on the PaaS product component information to generate a corresponding verification information.

The proprietary cloud server cluster is scanned through the proprietary cloud management platform and cluster management module to acquire a SaaS product component information of the proprietary cloud platform, including a virtual machine, a virtual storage, a virtual network, a PaaS service, a K8S service, a Pod, an API, a container, an application, a grouping, a container mirror image, etc. that support the product components, and the consistency and completeness verification is performed on the SaaS product component information to generate a corresponding verification information.

In operation S2114, a consistency and completeness verification is performed on all acquired information, and in response to the verification passing, a version information of the module or component is generated. The version information of the module or component may be generated based on an automatic generation rule of a version, such as an auto increment of a small-version version information; alternatively, the version information is determined manually, and the version information of a gene information of each module and component of the cluster is generated.

In operation S210, after the system hierarchical information of the first dimension is acquired, the association relationship information and the dependency relationship information of the module or component of the proprietary cloud sever cluster also need to be acquired.

In operation S212, the association relationship information is acquired. According to characteristics of each module and component, an arrangement information of each module and component in a tree component structure of the standard proprietary cloud platform is analyzed, and an information representation method is built based on hierarchies, such as a product line, a system, a module, a service, an application, a grouping, an instance, etc. For an extensible module, an expansion method and a representation method are determined. For example, a network node is added, and an IP, a port allocation mechanism, etc. are determined.

Figure 5A:
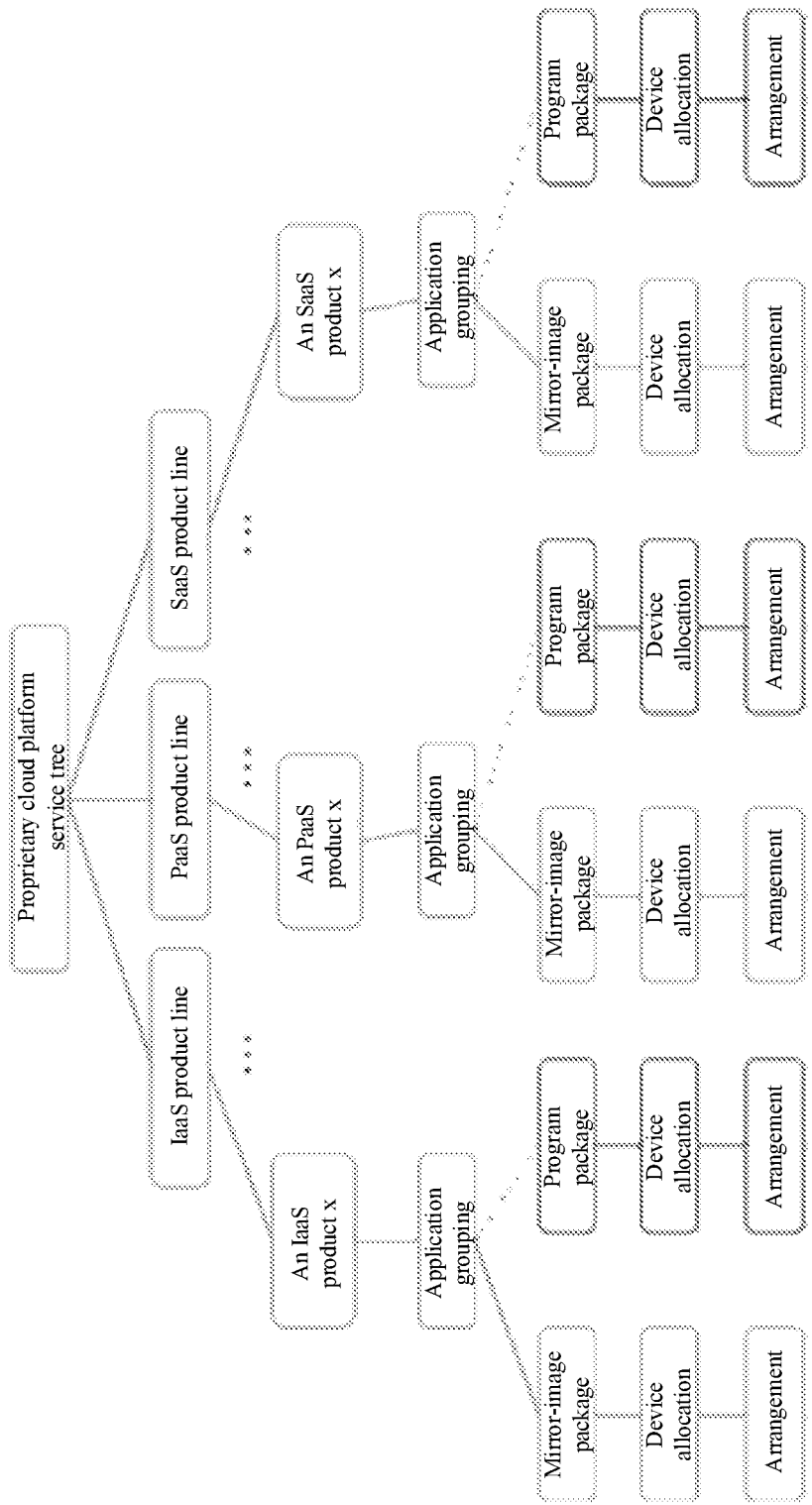
FIG. 5a schematically shows a schematic diagram of a proprietary cloud product line according to an embodiment of the present disclosure.

FIG. 5a schematically shows a schematic diagram of a proprietary cloud product line according to an embodiment of the present disclosure. As shown in FIG. 5a, the proprietary cloud platform includes an IaaS product line, a PaaS product line and a SaaS product line. Each product line includes a plurality of products, and each product is divided into a plurality of application groupings. The application groups may be built through an image-mirror package or application package.

Figure 5B:
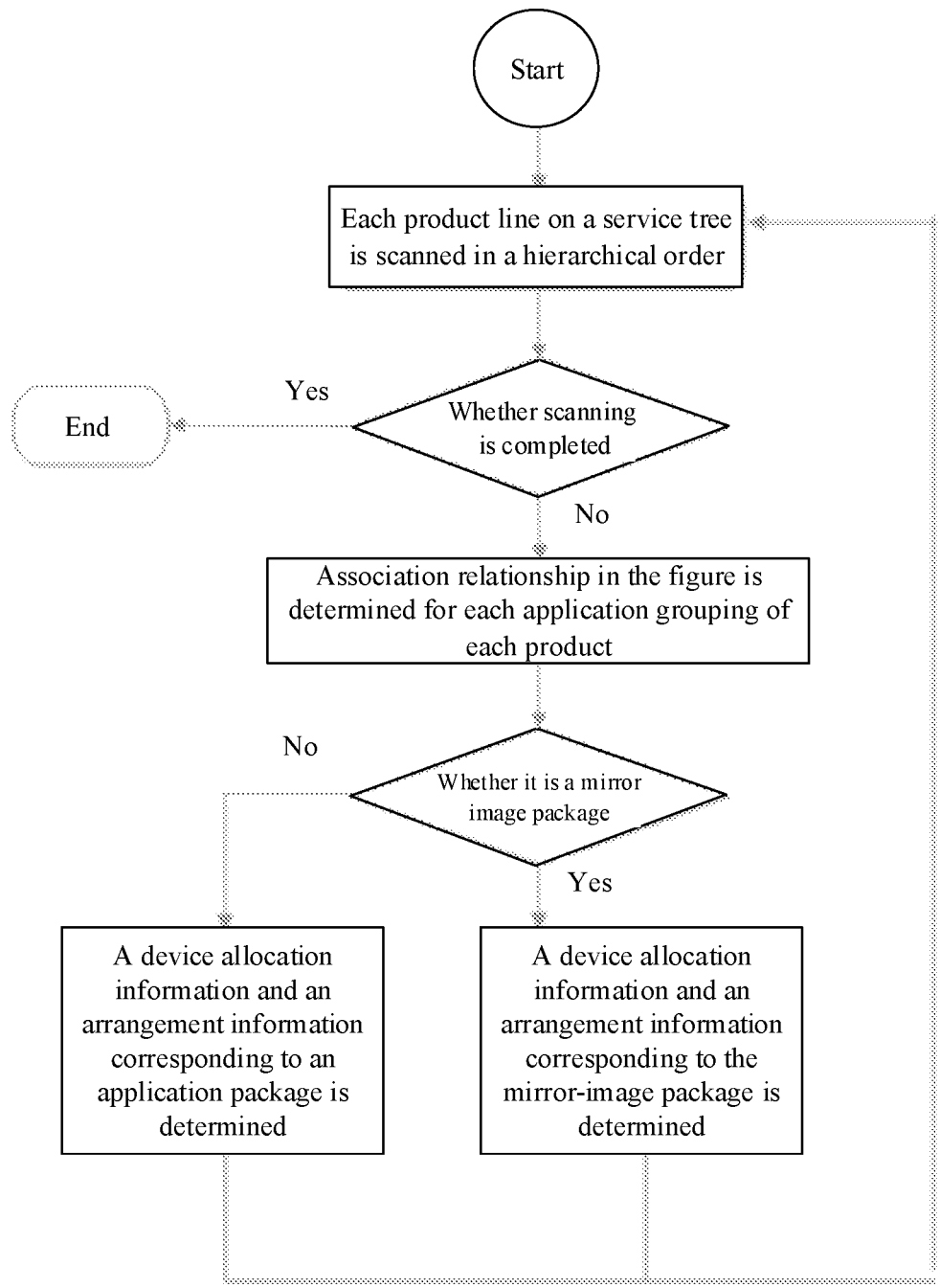
FIG. 5b schematically shows a flowchart of a method for acquiring and analyzing an association relationship information of a module or component of a proprietary cloud server cluster according to an embodiment of the present disclosure.

FIG. 5b schematically shows a flowchart of a method for acquiring and analyzing an association relationship information of a module or component of a proprietary cloud server cluster according to an embodiment of the present disclosure.

As shown in FIG. 5b, in operation S212, each proprietary cloud product line on a service tree is scanned in a hierarchical order of IaaS, PaaS, and SaaS. The method includes the following operations.

Each proprietary cloud product line of a proprietary cloud platform product line static service tree is scanned to acquire all proprietary cloud products of the proprietary cloud product line.

The proprietary cloud product is analyzed to determine an application grouping corresponding to the proprietary cloud product.

A creation unit of the application grouping is determined, and a device allocation information and an arrangement information of a corresponding container is determined according to the creation unit, wherein the creation unit is a mirror-image package or a program package. The device allocation information includes an SN number, a machine room, a rack, a server location, etc. After the analysis is completed, the process returns to scan a next proprietary cloud product line.

In operation S213, the dependency relationship information is acquired. A functional dependency relationship of each module and component in a process of building a standard proprietary cloud is analyzed, and it is required to ensure that an information of the dependent module and component when a cluster gene is built is ranked in front of a module on which the information depends during a serialization, so that a future instance generation is effective. When the dependency relationship is complex, a sequence of gene sequences is allowed to be manually adjusted according to a technical standard.

Specifically, in operation S213, the dependency relationship of an important module and component is analyzed for IaaS, PaaS, and SaaS service trees, so as to determine an order of a dependency chain. The method includes the following operations.

A proprietary cloud product line of a proprietary cloud platform product line static service tree is scanned to acquire all proprietary cloud products of the proprietary cloud product line.

An underlying function module information on which an application program of each proprietary cloud product related service depends and a function module information of a product having a dependency relationship with the application program are determined according to an information such as a reference statement contained in a program code, a reference statement of a configuration file, and a dependent component for data reading and writing, so as to acquire the dependency relationship.

Figure 6:
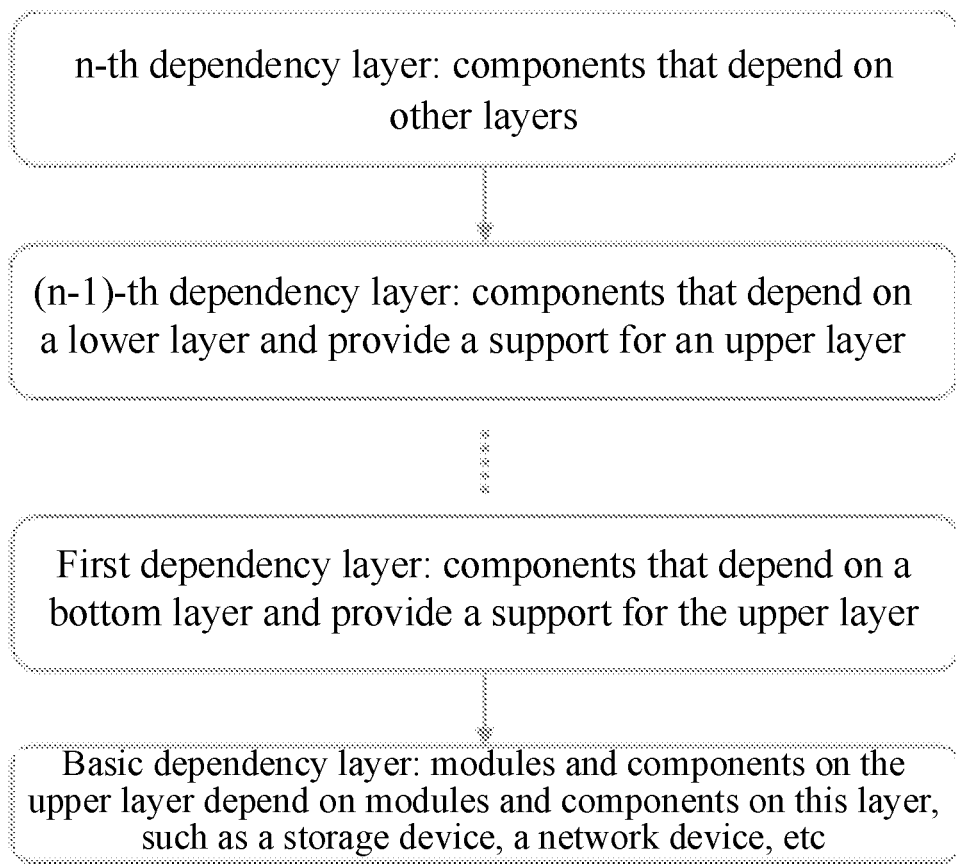
FIG. 6 schematically shows a flowchart of a method for acquiring and analyzing a dependency relationship information of a module or component of a proprietary cloud server cluster according to an embodiment of the present disclosure.

A set of corresponding dependent modules or dependent components is generated for each module or component; and a dependency hierarchy of all modules and components of a cloud platform is analyzed. FIG. 6 schematically shows a flowchart of a method for acquiring and analyzing a dependency relationship information of a module or component of a proprietary cloud server cluster according to an embodiment of the present disclosure. As shown in FIG. 6, a module and a component on an upper layer depend on a module and a component on a lower layer, and the module and the component on the same layer do not depend on each other.

In operation S220, the set of the gene information of the proprietary cloud container cluster is generated according to the acquired system hierarchical information, the acquired association relationship information and the acquired dependency relationship information of the module or component. Specifically, a cluster gene information system of three dimensions is built based on a system hierarchical information analysis, an association relationship analysis and a dependency relationship analysis of a proprietary cloud platform component:

1. An 8-hierarchical, discrete, and full coverage set of modules and components of the proprietary cloud cluster is generated through the system hierarchical information of the first dimension.
2. An association relationship set of each module and component of a product line on a basic component of the cluster is generated through the association relationship information of the second dimension.
3. A dependency relationship set of each module and component of a product line on an integration component of the cluster through the dependency relationship information of the third dimension.

Based on the above-mentioned three dimensions, a complete set of gene information of proprietary cloud cluster may be formed, and the integrity verification may be performed on the set of the gene information of the proprietary cloud container cluster. The integrity verification refers to a verification of effectiveness of a cluster gene information of each dimension at an overall system level. For example, whether the dependency relationship is accurate, and whether the module and component information is consistent and complete.

In operation S230, in response to the integrity verification passing, proprietary clouds of three dimensions are stored by using three database units based on the set of the gene information of the container cluster. In the first database unit, all system hierarchical information from the first layer to the eighth layer is stored sequentially; in the second database unit, based on a tree structure, such as a depth-first or breadth-first data structure, the cluster gene information of the second dimension is stored, and the association relationship set information of each module and component of a complete product line is saved; and in the third database unit, all components are stored based on the dependency relationship.

While persistently storing an extracted cluster gene information, it is also required to manage a gene version of the standard proprietary cloud to ensure that each valid standard proprietary cloud has a persistently stored cluster gene information version. When the version information is updated, a version is identified. The version information of the cluster gene information further includes that each module or component has its own version information.

Embodiments of the present disclosure may effectively perform a quick and accurate extraction on an overall information that may comprehensively describe a container cluster and a service application contained in the container cluster through an automated method. A method of expressing a gene information of a container cluster through three dimensions, which includes a system hierarchical dimension, a module association relationship dimension, and a module dependency dimension, may more accurately express an overall picture of the container cluster, and may be more conducive to a cluster replication based on genes.

In addition, for two deployment modes of a package deployment and a mirror-image deployment existing in a proprietary cloud, a cluster container gene detection-based information extraction technology proposed by embodiments of the present disclosure may uniformly process the two deployment modes.

Figure 7:
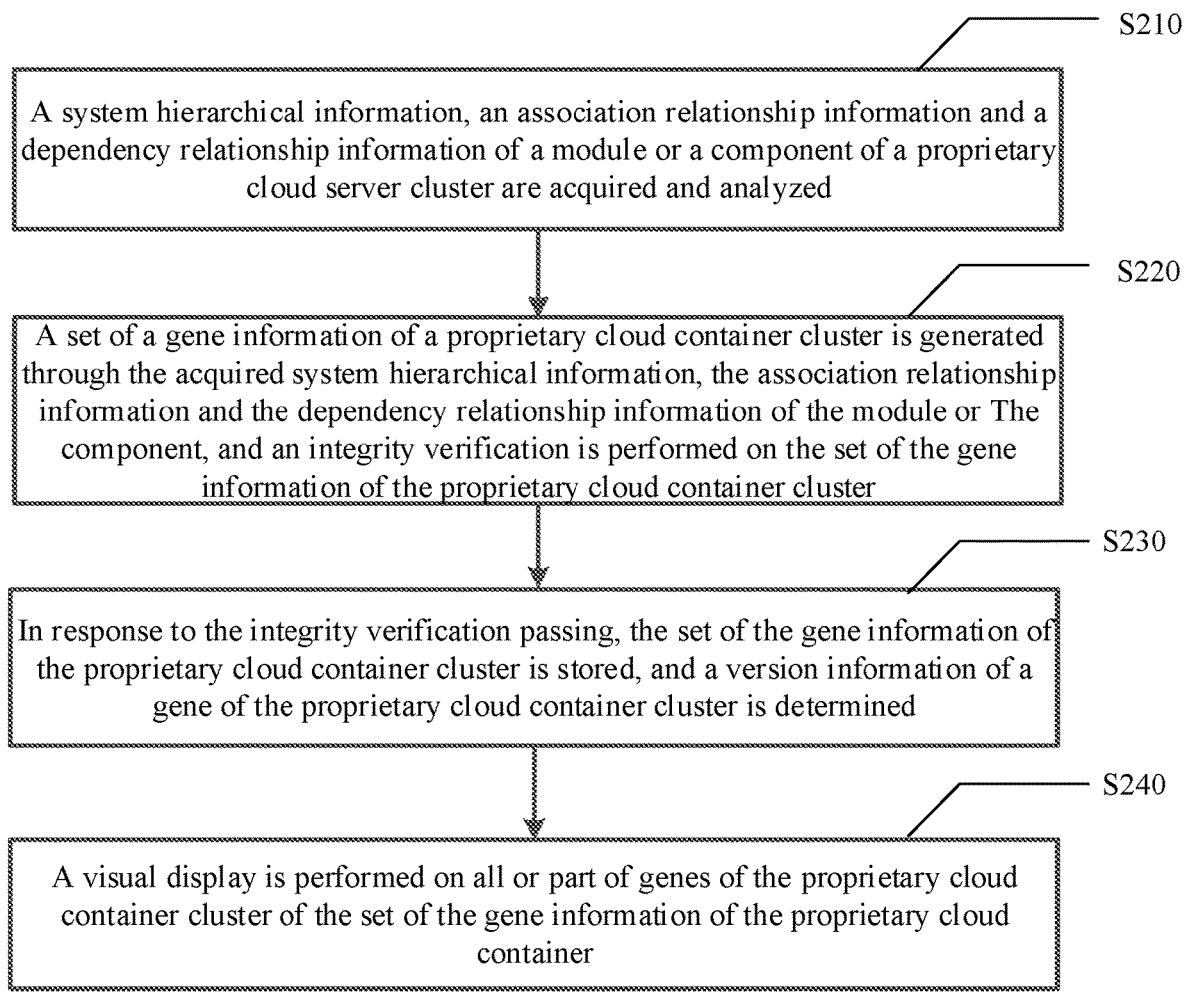
FIG. 7 schematically shows a flowchart of a method for acquiring a gene information of a proprietary cloud container cluster according to another embodiment of the present disclosure.

FIG. 7 schematically shows a flowchart of a method for acquiring a gene information of a proprietary cloud container cluster according to another embodiment of the present disclosure.

As shown in FIG. 7, different from the above-mentioned embodiments, after operation S230 of acquiring the gene information of the proprietary cloud container cluster, the method further includes operation S240.

In operation S240, a visual display is performed on all or part of genes of the proprietary cloud container cluster of the set of the gene information of the proprietary cloud container.

Specifically, based on the three dimensions of the cluster gene information, a display of the cluster gene information is also divided into three dimensions:

A name, a function, a technical indicator, a basic status and other information of each module and component of the cluster are comprehensively displayed according to 8 proprietaries of the system hierarchical information.

A service directory tree of the association relationship information is displayed through a tree structure, and a Pod information, a container information, and an application grouping information are displayed for each component.

A name and a status of each component of all dependency hierarchies in a proprietary cloud platform is displayed through a dependency hierarchical structure, and a module and a component on which a module and component depends are displayed, and which module and component the module or component provides a support for are displayed.

Embodiments of the present disclosure may effectively perform a quick and accurate extraction on an overall information that may comprehensively describe a container cluster and a service application contained in the container cluster through an automated method, and enable an extracted gene information to be effectively displayed, so as to provide a basis for a subsequent cluster generation and management based on the cluster gene information.

According to embodiments of the present disclosure, a problem of how to effectively perform a quick and accurate extraction on an overall information that may comprehensively describe a container cluster and a service application contained in the container cluster in a proprietary cloud container cluster environment by an automated method may be at least partially solved, and a technical effect of providing a basic basis for a subsequent cluster generation and management based on a cluster gene information may be implemented. At the same time, a problem of an inaccuracy of a standard proprietary cloud cluster structure and a deployment scheme during a proprietary cloud deployment may be solved, and an accuracy and an efficiency of the overall deployment of the automated cluster may be improved.

Figure 8:
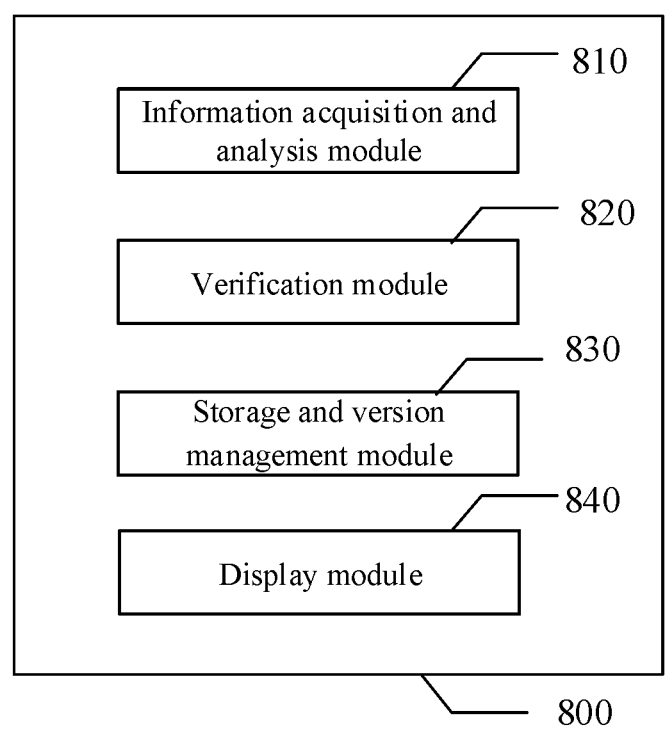
FIG. 8 schematically shows a block diagram of an apparatus for acquiring a gene information of a proprietary cloud container cluster according to an embodiment of the present disclosure.

FIG. 8 schematically shows a block diagram of an apparatus for acquiring a gene information of a proprietary cloud container cluster according to an embodiment of the present disclosure.

As shown in FIG. 8, an apparatus 800 for acquiring a gene information of a proprietary cloud container cluster includes an information acquisition and analysis module 810, a verification module 820, a storage and version management module 830, and a display module 840.

The information acquisition and analysis module 810 is used to acquire and analyze a system hierarchical information, an association relationship information and a dependency relationship information of a module or component of a proprietary cloud server cluster.

The verification module 820 is used to generate a set of a gene information of the proprietary cloud container cluster through the acquired system hierarchical information, the association relationship information and the dependency relationship information of the module or the component, and perform an integrity verification on the set of the gene information of the proprietary cloud container cluster.

The storage and version management module 830 is used to store the set of the gene information of the proprietary cloud container cluster, and determine a version information of a gene of the proprietary cloud container cluster.

In some embodiments, the apparatus further includes the display module 840 used to perform a visual display on all or part of genes of the proprietary cloud container cluster of the set of the gene information of the proprietary cloud container.

Any number of or at least some functions of any number of modules and units according to embodiments of the present disclosure may be implemented in a module. Any one or more of the modules and the units according to embodiments of the present disclosure may be split into a plurality of modules for implementation. Any one or more of the modules and the units according to embodiments of the present disclosure may be at least partially implemented as hardware circuits, such as a field programmable gate array (FPGA), a programmable logic array (PLA), a system on chip, a system on substrate, a system on package, a special integrated circuit (ASIC), or may be implemented by hardware or firmware in any other reasonable way of integrating or packaging a circuit, or may be implemented by any one or an appropriate combination of any number of three implementation methods of software, hardware and firmware. Alternatively, one or more of the modules and the units according to embodiments of the present disclosure may be at least partially implemented as a computer program module. The computer program module, when run, may perform a corresponding function.

For example, any number of the information acquisition and analysis module 810, the verification module 820, the storage and version management module 830 and the display module 840 may be combined in a module, or any one of the modules may be split into a plurality of modules. Alternatively, at least some functions of one or more of the modules may be combined with at least some functions of other modules and implemented in a module. According to embodiments of the present disclosure, at least one of the information acquisition and analysis module 810, the verification module 820, the storage and version management module 830 and the display module 840 may be at least partially implemented as a hardware circuit, such as a field programmable gate array (FPGA), a programmable logic array (PLA), a system on chip, a system on substrate, a system on package, or an application specific integrated circuit (ASIC), or may be implemented by hardware or firmware in any other reasonable way of integrating or encapsulating the circuit, or may be implemented by any one or an appropriate combination of any number of the three implementation methods of software, hardware and firmware. Alternatively, at least one of the information acquisition and analysis module 810, the verification module 820, the storage and version management module 830 and the display module 840 may be at least partially implemented as a computer program module. The computer program module, when run, may perform a corresponding function.

Figure 9:
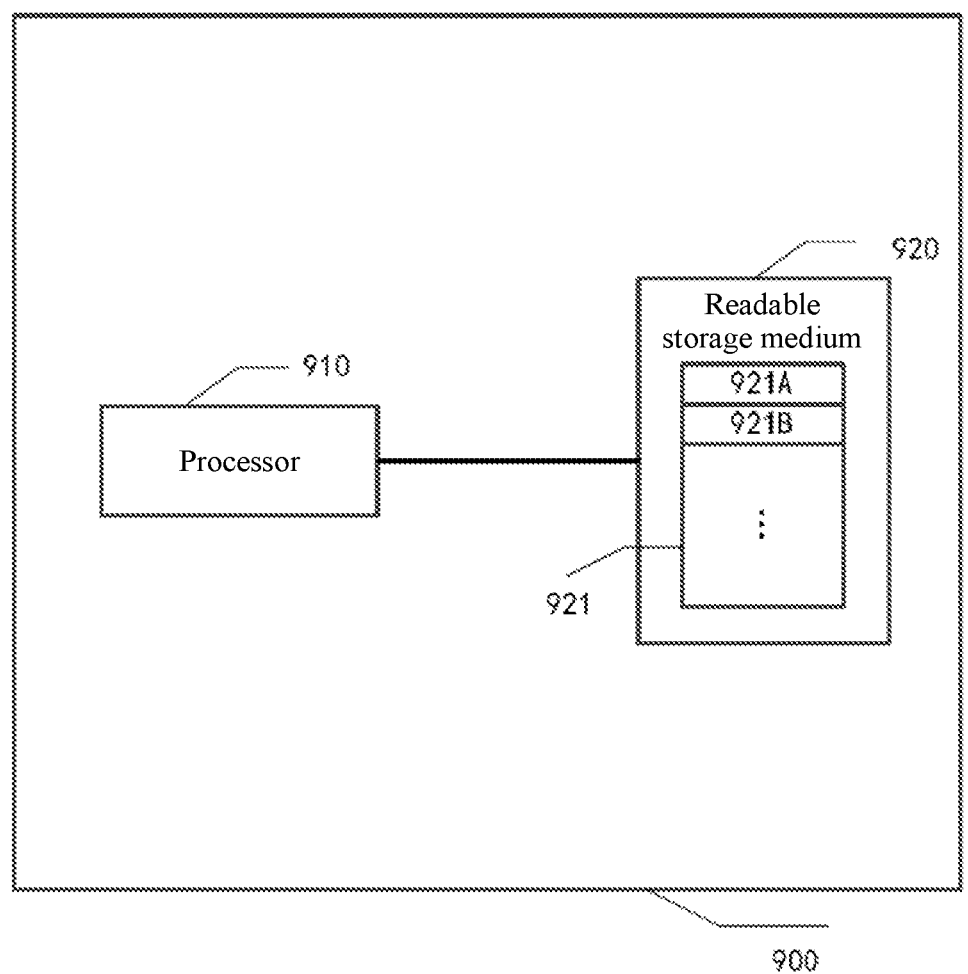
FIG. 9 schematically shows a block diagram of an electronic device according to an embodiment of the present disclosure.

FIG. 9 schematically shows a block diagram of an electronic device according to an embodiment of the present disclosure. The electronic device shown in FIG. 9 is only an example, which is not intended to limit a function and a scope of use of embodiments of the present disclosure.

As shown in FIG. 9, an electronic device 900 includes a processor 910 and a computer-readable storage medium 920. The electronic device 900 may perform the method according to embodiments of the present disclosure.

Specifically, the processor 910 may include, for example, a general-purpose microprocessor, an instruction set processor, and/or a related chipset and/or a dedicated-purpose microprocessor (e.g., an application specific integrated circuit (ASIC)), etc. The processor 910 may also include an on-board memory for a caching purpose. The processor 910 may be a single processing unit or a plurality of processing units used to perform different actions of a method flow according to embodiments of the present disclosure.

For example, the computer-readable storage medium 920 may be a nonvolatile computer-readable storage medium. Specific examples of the computer-readable storage medium 920 include, but are not limited to: a magnetic storage device, such as a magnetic tape or hard disk (HDD); an optical storage device, such as an optical disc (CD-ROM); a memory, such as a random access memory (RAM) or flash memory; etc.

The computer-readable storage medium 920 may include a computer program 921, and the computer program 921 may include codes/computer executable instructions which, when executed by the processor 910, cause the processor 910 to perform the method according to embodiments of the present disclosure or any variation thereof.

For example, the computer program 921 may be configured to have a computer program code including a computer program module. For example, in an exemplary embodiment, the codes of the computer program 921 may include one or more program modules, such as a module 921A, a module 921B, . . . . It should be noted that a division method and a number of modules are not fixed, and those skilled in the art may use appropriate program modules or program module combinations according to an actual situation. The program module combinations, when executed by the processor 910, cause the processor 910 to perform the method according to embodiments of the present disclosure or any variation thereof.

According to embodiments of the present disclosure, at least one of the information acquisition and analysis module 810, the verification module 820, the storage and version management module 830 and the display module 840 may be implemented as a computer program module described with reference to FIG. 9. The computer program module, when executed by the processor 910, may implement the corresponding operations as described above.

The present disclosure further provides a computer-readable storage medium, and the computer-readable storage medium may be contained in the device/apparatus/system described in the above-mentioned embodiments; the computer-readable storage medium may also exist alone without being assembled into the device/apparatus/system. The above-mentioned computer-readable storage medium carries one or more programs. The one or more programs, when executed, implement the method according to embodiments of the present disclosure.

The flowcharts and the block diagrams in the accompanying drawings illustrate an architecture, a function and an operation, which are possibly implemented, of the system, the method and the computer program product according to various embodiments of the present disclosure. In this regard, each block in the flowcharts or the block diagrams may represent a module, a program segment, or a portion of a code, and the module, the program segment, or the portion of the code contains one or more executable instructions for implementing a specified logical function. It should also be noted that, in some alternative implementations, functions marked in the block may also occur in a different order from those marked in the accompanying drawings. For example, two consecutive blocks may actually be executed substantially in parallel, or they may sometimes be executed in a reverse order, which depends on functions involved. It should also be noted that each block in the block diagrams or flowcharts, and a combination of blocks in the block diagrams or flowcharts may be implemented with a dedicated hardware-based system that performs a specified function or operation, or may be implemented with a combination of a dedicated hardware and a computer instruction.

Those skilled in the art may understand that although the present disclosure has been shown and described with reference to specific exemplary embodiments of the present disclosure, those skilled in the art should understand that the present disclosure may be changed in form and detail without departing from the spirit and scope of the present disclosure defined by the appended claims and their equivalents. Therefore, the scope of the present disclosure should not be limited to the above-mentioned embodiments, but should be determined by not only the appended claims, but also equivalents of the appended claims.

What is claimed is:

1. A method for acquiring a gene information of a proprietary cloud container cluster, comprising:
    acquiring and analyzing a system hierarchical information, an association relationship information and a dependency relationship information of a module or a component of a proprietary cloud server cluster;
    generating a set of a gene information of a proprietary cloud container cluster through the acquired system hierarchical information, the association relationship information and the dependency relationship information of the module or the component, and performing an integrity verification on the set of the gene information of the proprietary cloud container cluster; and
    storing the set of the gene information of the proprietary cloud container cluster and determining a version information of a gene of the proprietary cloud container cluster, in response to the integrity verification passing,
    wherein the acquiring and analyzing a system hierarchical information of a module or a component of a proprietary cloud server cluster comprises:
    acquiring and analyzing a basic system gene information of the proprietary cloud server cluster, and verifying the basic system gene information to generate a verification information;
    acquiring and analyzing a basic dependent gene information of the proprietary cloud server cluster, and verifying the basic dependent gene information to generate a verification information;
    acquiring and analyzing a product line static service tree gene information of the proprietary cloud server cluster, and verifying the product line static service tree gene information to generate a verification information; and
    performing a consistency and completeness verification on all acquired information, and generating, in response to the verification passing, a version information of the module or the component.

2. The method according to claim 1, further comprising: performing a visual display on all or part of genes of the proprietary cloud container cluster of the set of the gene information of the proprietary cloud container.

3. The method according to claim 2, wherein the performing a visual display on all or part of genes of the proprietary cloud container cluster of the set of the gene information of the proprietary cloud container comprises:
    displaying the system hierarchical information of the proprietary cloud server cluster in order of the basic system gene information, the basic dependency gene information, and the product line static service tree gene information, wherein the system hierarchical information comprises a name, a function, a technical indicator, and a basic status information of the module or the component;
    displaying a service directory tree of the association relationship information by using a tree structure, and displaying a container information, and an application grouping information of the module or the component; and
    displaying, through a dependency hierarchical structure, a name and a status of each component of all dependency hierarchies in a proprietary cloud platform and a module and a component on which the module or the component depends, and displaying a module or component for which the module or the component provides a support.

4. The method according to claim 1, wherein the acquiring and analyzing a basic system gene information of the proprietary cloud server cluster, and verifying the basic system gene information to generate a verification information comprises:

scanning the proprietary cloud server cluster through an out-of-band management system and an in-band management system to acquire a gene information of a physical server cluster, and performing a consistency and completeness verification on the gene information of the physical server cluster to generate a corresponding verification information;

scanning the proprietary cloud server cluster through a cloud platform operation and maintenance management system to acquire an operating system and network topology information, and performing the consistency and completeness verification on the operating system and network topology information to generate a corresponding verification information; and scanning the proprietary cloud server cluster through the cloud platform operation and maintenance management system to acquire a cluster component information, and performing the consistency and completeness verification on the cluster component information to generate a corresponding verification information.

5. The method according to claim 1, wherein the acquiring and analyzing a basic dependent gene information of the proprietary cloud server cluster, and verifying the basic dependent gene information to generate a verification information comprises:

scanning the proprietary cloud server cluster through a cloud platform operation and maintenance management system to acquire a dependent component information of a proprietary cloud platform product line, and performing a consistency and completeness verification on the dependent component information to generate a corresponding verification information.

6. The method according to claim 1, wherein the acquiring and analyzing a product line static service tree gene information of the proprietary cloud server cluster, and verifying the product line static service tree gene information to generate a verification information comprises:

scanning the proprietary cloud server cluster through a proprietary cloud management platform and cluster management module to acquire an IaaS product component information of a proprietary cloud platform, and performing a consistency and completeness verification on the IaaS product component information to generate a corresponding verification information;

scanning the proprietary cloud server cluster through the proprietary cloud management platform and cluster management module to acquire a PaaS product component information of the proprietary cloud platform, and performing the consistency and completeness verification on the PaaS product component information to generate a corresponding verification information; and scanning the proprietary cloud server cluster through the proprietary cloud management platform and cluster management module to acquire a SaaS product component information of the proprietary cloud platform, and performing the consistency and completeness verification on the SaaS product component information to generate a corresponding verification information, wherein the IaaS is a cloud platform service layer that comprises basic cloud resources comprising a virtualized computing resource, a virtualized network resource, and a virtualized storage resource; the PaaS is a cloud platform service layer that provides platform level cloud resources comprising a database, a middleware, a development component, and a big data component; and the SaaS is a cloud platform service layer that provides a software resource to support a specific business.

7. The method according to claim 1, wherein the acquiring and analyzing an association relationship information of a module or a component of a proprietary cloud server cluster comprises:

scanning an IaaS product line, a PaaS product line and a SaaS product line of a proprietary cloud platform product line static service tree to acquire all proprietary cloud products of the IaaS product line, the PaaS product line and the SaaS product line;

analyzing the proprietary cloud product to determine an application grouping corresponding to the proprietary cloud product; and determining a creation unit of the application grouping, and determining a device allocation information and an arrangement information of a corresponding container according to the creation unit, wherein the creation unit is a mirror-image package or a program package, wherein the IaaS is a cloud platform service layer that comprises basic cloud resources comprising a virtualized computing resource, a virtualized network resource, and a virtualized storage resource; the PaaS is a cloud platform service layer that provides platform level cloud resources comprising a database, a middleware, a development component, and a big data component; and the SaaS is a cloud platform service layer that provides a software resource to support a specific business.

8. The method according to claim 1, wherein the acquiring and analyzing a dependency relationship information of a module or component of a proprietary cloud server cluster comprises:

scanning an IaaS product line, a PaaS product line and a SaaS product line of a proprietary cloud platform product line static service tree to acquire all proprietary cloud products of the IaaS product line, the PaaS product line and the SaaS product line;

determining, according to a reference statement contained in a program code, a reference statement of a configuration file, and a dependent component information for data reading and writing, an underlying function module information on which an application program of each proprietary cloud product related service depends and a function module information of a product having a dependency relationship with the application program, so as to acquire a dependency relationship;

generating, for each module or component, a set of corresponding dependent modules or dependent components; and analyzing a dependency hierarchy of the module or component according to the dependency relationship, wherein the IaaS is a cloud platform service layer that comprises basic cloud resources comprising a virtualized computing resource, a virtualized network resource, and a virtualized storage resource; the PaaS is a cloud platform service layer that provides platform level cloud resources comprising a database, a middleware, a development component, and a big data component; and the SaaS is a cloud platform service layer that provides a software resource to support a specific business.

9. The method according to claim 1, wherein storing the system hierarchical information comprises:
storing the system hierarchical information to a first database in order of the basic system gene information, the basic dependent gene information and the product line static service tree gene information;
storing the association relationship information to a second database based on a tree data structure; and
storing the dependency relationship information in a third database.

10. An electronic device, comprising:
one or more processors;
a storage apparatus configured to store one or more programs,
wherein the one or more programs, when executed by the one or more processors, cause the one or more processors to perform the method for acquiring a gene information of a proprietary cloud container cluster according to claim 1.

11. A non-transitory computer-readable storage medium having executable instructions stored thereon, wherein the instructions, when executed by a processor, cause the processor to perform the method for acquiring a gene information of a proprietary cloud container cluster according to claim 1.

12. An apparatus for acquiring a gene information of a proprietary cloud container cluster, comprising:
an information acquisition and analysis module configured to acquire and analyze a system hierarchical information, an association relationship information and a dependency relationship information of a module or a component of a proprietary cloud server cluster;
a verification module configured to generate a set of a gene information of a proprietary cloud container cluster through the acquired system hierarchical information, the association relationship information and the dependency relationship information of the module or the component, and perform an integrity verification on the set of the gene information of the proprietary cloud container cluster; and
a storage and version management module configured to store the set of the gene information of the proprietary cloud container cluster and determine a version information of a gene of the proprietary cloud container cluster, in response to the integrity verification passing,
wherein the information acquisition and analysis module is further configured to:
acquire and analyze a basic system gene information of the proprietary cloud server cluster, and verify the basic system gene information to generate a verification information;
acquire and analyze a basic dependent gene information of the proprietary cloud server cluster, and verify the basic dependent gene information to generate a verification information;
acquire and analyze a product line static service tree gene information of the proprietary cloud server cluster, and verify the product line static service tree gene information to generate a verification information; and
perform a consistency and completeness verification on all acquired information, and generate, in response to the verification passing, a version information of the module or the component.

13. The apparatus according to claim 12, further comprising:
a display module configured to perform a visual display on all or part of genes of the proprietary cloud container cluster of the set of the gene information of the proprietary cloud container.

* * * * *